United States Patent
Terahara et al.

(10) Patent No.: US 10,517,907 B2
(45) Date of Patent: Dec. 31, 2019

(54) ANTICARIOGENIC AGENT AND ANTICARIOGENIC COMPOSITION

(71) Applicant: Meiji Co., Ltd., Tokyo (JP)

(72) Inventors: Masaki Terahara, Kanagawa (JP); Takeshi Takahashi, Kanagawa (JP); Hiroyuki Itou, Kanagawa (JP)

(73) Assignee: Meiji Co., Ltd., Tokyo (JP)

( * ) Notice: Subject to any disclaimer, the term of this patent is extended or adjusted under 35 U.S.C. 154(b) by 0 days.

(21) Appl. No.: 16/353,678

(22) Filed: Mar. 14, 2019

(65) Prior Publication Data

US 2019/0201460 A1 Jul. 4, 2019

Related U.S. Application Data

(63) Continuation of application No. 15/560,375, filed as application No. PCT/JP2016/065242 on May 24, 2016, now abandoned.

(30) Foreign Application Priority Data

May 29, 2015 (JP) ................................. 2015-110743

(51) Int. Cl.

| A61K 35/745 | (2015.01) |
| A61Q 11/00 | (2006.01) |
| A61K 47/36 | (2006.01) |
| A61K 9/16 | (2006.01) |
| C12N 1/20 | (2006.01) |
| A23L 33/135 | (2016.01) |
| A61K 8/99 | (2017.01) |

(52) U.S. Cl.
CPC .......... *A61K 35/745* (2013.01); *A23L 33/135* (2016.08); *A61K 8/99* (2013.01); *A61K 9/16* (2013.01); *A61K 47/36* (2013.01); *A61Q 11/00* (2013.01); *C12N 1/20* (2013.01); *A23V 2002/00* (2013.01)

(58) Field of Classification Search
None
See application file for complete search history.

(56) References Cited

U.S. PATENT DOCUMENTS

| 2006/0018843 A1 | 1/2006 | Fine |
| 2009/0142374 A1 | 6/2009 | Moro et al. |
| 2012/0114701 A1 | 5/2012 | Petit et al. |

FOREIGN PATENT DOCUMENTS

| JP | 11-12143 A | 1/1999 |
| JP | 2000-281550 A | 10/2000 |
| JP | 2003-171292 A | 6/2003 |
| JP | 2008-182931 A | 8/2008 |
| JP | 2011-201840 A | 10/2011 |
| JP | 2012-526752 A | 11/2012 |
| RU | 2558934 C1 * | 8/2015 |
| RU | 2580615 C1 * | 4/2016 |
| WO | 2006/087913 A1 | 8/2006 |
| WO | 2007/020884 A1 | 2/2007 |
| WO | 2010/130663 A1 | 11/2010 |

OTHER PUBLICATIONS

Liu et al. PLOS ONE 8: e78723, pp. 1-6, 2013.*
Gati et al. International J. Dentistry 2011: pp. 1-6, 2011.*
Silk et al. Am. Family Physician 77: 1139-1144, 2008.*
Iakushenko et al. Zh Mikrobiol. Epidemiol. Immunobiol. 6: 18-22, 1997, abstract.*
Google translation of RU 2580615 C1, pp. 1-8, 2015.*
Google translation of RU 2558934 C1, pp. 1-10, 2015.*
Communication dated Jan. 10, 2019, issued by the European Patent Office in counterpart European Patent Application No. 16803127.6.
Communication dated Nov. 8, 2018, issued by the Pakistanian Patent Office in counterpart Pakistan Application No. 286/2016.
International Search Report, issued by International Searching Authority in corresponding International Application No. PCT/JP2016/065242, dated Aug. 16, 2016, (PCT/ISA/210).
Nakamura, et al., Upregulation of Polymeric Immunoglobulin Receptor Expression by the Heat-Inactivated Potential Probiotic Bifidobacterium bifidum 0LB6378 in a Mouse Intestinal Explant Model, 2011, Scandinavian Journal of Immunology, pp. 176-183, XP-002787451.
Ohno et al., Oral Administration of Bifidobacterium bifidum G9-1 SuppressesTotal and Antigen Specific Immunoglobulin E Production in Mice, Biol. Pharm. Bull, vol. 28, No. 8, Aug. 2005, pp. 1462-1466 (5 total pages).
Search Report dated Aug. 21, 2018, issued by the Intellectual Property Office of Singapore in counterpart Singaporean Application No. 11201707793Y.
Written Opinion dated Aug. 21, 2018, issued by the Intellectual Property Office of Singapore in counterpart Singaporean Application No. 11201707793Y.
Written Opinion, issued by International Searching Authority in corresponding International Application No. PCT/JP2016/065242, dated Aug. 16, 2016, (PCT/ISA/237).

* cited by examiner

*Primary Examiner* — Sarvamangala Devi
(74) *Attorney, Agent, or Firm* — Sughrue Mion, PLLC

(57) ABSTRACT

The present invention provides a novel anticariogenic agent without side effects so that anticariogenic effect can also be obtained in humans who are highly sensitive to oligosaccharides and sugar alcohols. Also, an agent for preventing periodontal disease or for treating periodontal disease which has an effect of preventing or treating periodontal disease and which does not have side effects is provided. The invention relates to an anticariogenic agent and an anticariogenic composition comprising a bifidobacterium, an agent and a composition for preventing periodontal disease comprising a bifidobacterium and an agent and a composition for treating periodontal disease comprising a bifidobacterium.

9 Claims, No Drawings

Specification includes a Sequence Listing.

SEQUENCE LISTING

```
<160> NUMBER OF SEQ ID NOS: 4

<210> SEQ ID NO 1
<211> LENGTH: 20
<212> TYPE: DNA
<213> ORGANISM: Bifidobacterium bifidum

<400> SEQUENCE: 1
ccacatgatc gcatgtgatt                                              20

<210> SEQ ID NO 2
<211> LENGTH: 19
<212> TYPE: DNA
<213> ORGANISM: Bifidobacterium bifidum

<400> SEQUENCE: 2
ccgaaggctt gctcccaaa                                               19

<210> SEQ ID NO 3
<211> LENGTH: 20
<212> TYPE: DNA
<213> ORGANISM: Bifidobacterium longum

<400> SEQUENCE: 3
ttccagttga tcgcatggtc                                              20

<210> SEQ ID NO 4
<211> LENGTH: 20
<212> TYPE: DNA
```

```
<213> ORGANISM: Bifidobacterium longum

<400> SEQUENCE: 4
gggaagccgt atctctacga                                               20
```

ANTICARIOGENIC AGENT AND ANTICARIOGENIC COMPOSITION

CROSS-REFERENCE TO RELATED APPLICATIONS

This application is a Continuation Application of U.S. application Ser. No. 15/560,375, filed Sep. 21, 2017, which is a National Stage of International Application No. PCT/JP2016/065242, filed May 24, 2016, which claims priority from Japanese Patent Application No. 2015-110743, filed May 29, 2015, the contents of all of which are incorporated herein by reference in their entirety.

TECHNICAL FIELD

The present invention relates to an anticariogenic agent and an anticariogenic composition containing a bifidobacterium.

BACKGROUND ART

Dental caries develops when cariogenic bacteria living in the oral cavity, such as *Streptococcus mutans*, take cariogenic carbohydrates contained in foods and drinks, such as sucrose, fructose and glucose, and produce acids, and the acids dissolve enamel and dentine of the tooth surface.

The main components of enamel and dentine of the tooth surface are hydroxyapatite and fluororapatite. These substances are decomposed by the activities of the acids produced by the cariogenic bacteria, and phosphate ion and calcium ion are released (demineralization).

At the same time, calcium ion and phosphate ion in saliva in the oral cavity are incorporated into the enamel surface, and the demineralized part is recrystallized (remineralization).

Demineralization and remineralization are repeated in the oral cavity at every meal and are generally in an equilibrium state. Dental caries develops when the balance is disturbed.

As means for preventing dental caries, use of oligosaccharides, sugar alcohols or the like having anticariogenic activity is known. In Patent Document 1, palatinit is used as a noncariogenic oligosaccharide which is not consumed by mutans streptococci. Patent Document 2 discloses one, or two or more sugar alcohols selected from xylitol, mannitol, galactitol and inositol and describes that the sugar alcohols have anticariogenic activity.

RELATED ART DOCUMENTS

Patent Documents

[Patent Document 1] JP-A-2000-281550
[Patent Document 2] JP-A-11-12143

SUMMARY OF THE INVENTION

Problems that the Invention is to Solve

However, the oligosaccharide and the sugar alcohols above are apt to cause diarrhea, dehydration or the like in some humans due to the individual differences in intestinal sensitivity, and thus there are problems that oligosaccharides or sugar alcohols cannot be provided to such humans.

Therefore, an object of the invention is to provide a novel anticariogenic agent without side effects so that anticariogenic effect can also be obtained in humans who are highly sensitive to oligosaccharides and sugar alcohols.

Another object of the invention is to provide an agent for preventing periodontal disease or for treating periodontal disease which has an effect of preventing or treating periodontal disease and which does not have side effects.

Means for Solving the Problems

The present inventors have focused on a bacterium belonging to genus *Bifidobacterium* (i.e., a bifidobacterium) as candidates for a novel anticariogenic agent. *Bifidobacterium* has been known as enteric bacteria which are useful from both nutritional and bacteriological points of view because *Bifidobacterium* has effects such as the improvement of diarrhea, the improvement of constipation, the prevention or the treatment of opportunistic bacterium infections and pathogenic microorganism infections, the inhibition of the growth of harmful enteric bacteria, the production of B vitamins and the facilitation of digestion and absorption by decomposing lactose. Also, *Bifidobacterium* has been known to have an effect on the host intestinal immune system, an improvement effect on allergies and the like.

As a result of intensive investigations, the inventors have found that a bifidobacterium has anticariogenic effect by itself, and achieved the invention. The inventors also found that a bifidobacterium has an effect of preventing or treating periodontal disease by themselves.

Therefore, the invention is as follows.

1. An anticariogenic agent comprising a bifidobacterium.
2. The anticariogenic agent according to the item 1 above, wherein the bifidobacterium is *Bifidobacterium bifidum*.
3. The anticariogenic agent according to the item 1 or 2 above, wherein the bifidobacterium is *Bifidobacterium bifidum* OLB6378 strain (accession number: NITE BP-31).
4. The anticariogenic agent according to any one of the items 1 to 3 above, wherein the bifidobacterium is in the form of heat-treated cell.
5. The anticariogenic agent according to any one of the items 1 to 4 above, wherein the bifidobacterium is applied in an amount of $10^8$ cells/day or more continuously for four weeks or longer.
6. An anticariogenic composition comprising the anticariogenic agent according to any one of the items 1 to 5 above.
7. The anticariogenic composition according to the item 6 above further comprising a dispersant.
8. The anticariogenic composition according to the item 7 above, wherein the dispersant is dextrin.
9. The anticariogenic composition according to any one of the items 6 to 8 above, which is an anticariogenic food composition.
10. The anticariogenic composition according to any one of the items 6 to 8 above, which is an anticariogenic pharmaceutical composition.
11. An oral preparation comprising the anticariogenic composition according to the item 10 above.
12. A package comprising the anticariogenic composition according to any one of the items 6 to 10 above and a packaging material, wherein the anticariogenic composition is packaged in the packaging material.
13. An agent for preventing periodontal disease or an agent for treating periodontal disease, which comprises a bifidobacterium.
14. An anticariogenic agent, an agent for preventing periodontal disease or an agent for treating periodontal disease, which comprises a bifidobacterium.

15. *Bifidobacterium bifidum* OLB6378 strain (accession number: NITE BP-31) which has been heat treated.

Advantage of the Invention

In the invention, it was found that a bifidobacterium has anticariogenic effect, and thus it has become possible to provide a novel anticariogenic agent or anticariogenic composition containing a bifidobacterium and without side effects.

Also, because it was found that a bifidobacterium has an effect of preventing or treating periodontal disease, it has become possible to provide a novel agent for preventing periodontal disease or for treating periodontal disease containing a bifidobacterium and without side effects or a novel composition for preventing periodontal disease or for treating periodontal disease containing a bifidobacterium and without side effects.

MODE FOR CARRYING OUT THE INVENTION

The invention is explained in detail below.

The invention relates to an anticariogenic agent or an anticariogenic composition containing a bifidobacterium.

The invention also relates to an agent for preventing periodontal disease or for treating periodontal disease containing a bifidobacterium or a composition for preventing periodontal disease or for treating periodontal disease containing a bifidobacterium.

In the present specification, unless otherwise specifically noted, the anticariogenic agent, the agent for preventing periodontal disease and the agent for treating periodontal disease are together referred to as "the agent of the invention", and the anticariogenic composition, the composition for preventing periodontal disease and the composition for treating periodontal disease are together referred to as "the composition of the invention".

<Bifidobacterium>

The bifidobacterium used for the invention is a bacterium belonging to genus *Bifidobacterium*, and the kind and the origin of the bifidobacterium used for the invention are not limited. Specifically, examples of the bifidobacterium include *Bifidobacterium bifidum*, *Bifidobacterium longum*, *Bifidobacterium breve*, *Bifidobacterium adolescentis*, *Bifidobacterium infantis*, *Bifidobacterium pseudolongum*, *Bifidobacterium lactis* and *Bifidobacterium thermophilum*.

A specific example of the strain of *Bifidobacterium bifidum* is *Bifidobacterium bifidum* OLB6378 strain (accession number: NITE BP-31). Examples of the strain of *Bifidobacterium longum* include *Bifidobacterium longum* No. 7 strain (accession number: FERM BP-11242) and *Bifidobacterium longum* OLB6290 strain (accession number: NITE P-75). It has become possible to provide the agent of the invention using these strains.

The applicant has deposited these strains in National Institute of Technology and Evaluation, NITE Patent Microorganisms Depositary, or in National Institute of Advanced Industrial Science and Technology, International Patent Organism Depositary. The contents that specify the deposited strains are described below.

The applicant has deposited *Bifidobacterium bifidum* OLB6378 strain under the following conditions.
(1) Name of Depositary Authority:
    National Institute of Technology and Evaluation, NITE Patent Microorganisms Depositary
(2) Contact:
    2-5-8 Kazusakamatari, Kisarazu-shi, Chiba 292-0818
    (Present Address: 122, 2-5-8 Kazusakamatari, Kisarazu-shi, Chiba 292-0818)
    Phone number: 0438-20-5580
(3) Accession Number:
    NITE BP-31
(4) Identification Indication:
    *Bifidobacterium bifidum* OLB6378
(5) Date of Original Deposit:
    Oct. 26, 2004
(6) Date of Transfer to an International Deposit Under the Budapest Treaty:
    Jan. 18, 2006

The applicant has deposited *Bifidobacterium longum* No. 7 strain under the following conditions.
(1) Name of Depositary Authority:
    National Institute of Advanced Industrial Science and Technology, International Patent Organism Depositary (Name of present depositary authority: National Institute of Technology and Evaluation, NITE Patent Microorganisms Depositary)
(2) Contact:
    Central 6, 1-1-1 Higashi, Tsukuba, Ibaraki 305-8566
    Phone number: 029-861-6029
    (Present Contact:
    120, 2-5-8 Kazusakamatari, Kisarazu-shi, Chiba 292-0818
    Phone number: 0438-20-5910)
(3) Accession Number:
    FERM BP-11242
(4) Identification Indication:
    *Bifidobacterium longum* No. 7
(5) Date of Original Deposit:
    Apr. 20, 1993
(6) Date of Transfer to an International Deposit Under the Budapest Treaty:
    Mar. 2, 2010

The applicant has deposited *Bifidobacterium longum* OLB6290 strain under the following conditions.
(1) Name of Depositary Authority:
    National Institute of Technology and Evaluation, NITE Patent Microorganisms Depositary
(2) Contact:
    2-5-8 Kazusakamatari, Kisarazu-shi, Chiba 292-0818
    (Present Address: 122, 2-5-8 Kazusakamatari, Kisarazu-shi, Chiba 292-0818)
    Phone number: 0438-20-5580
(3) Accession Number:
    NITE P-75
(4) Identification Indication:
    *Bifidobacterium longum* OLB6290
(5) Date of Deposit:
    Feb. 3, 2005

*Bifidobacterium bifidum* OLB6378 strain, *Bifidobacterium longum* No. 7 strain and *Bifidobacterium longum* OLB6290 strain have the following mycological properties.

*Bifidobacterium bifidum* OLB6378 strain is a gram-positive, obligately anaerobic, rod-shaped bacterium isolated from human infant feces. When this bacterium is cultured on a BL agar (Eiken Chemical Co., Ltd.) plate at 37° C. for 48 hours under anaerobic conditions using AnaeroPack•Kenki (manufactured by Mitsubishi Gas Chemical Company, Inc.), opaque, circular, hemisphere, glossy colonies are formed.

Also, a PCR product is obtained by PCR using *Bifidobacterium bifidum*-specific primers (Proceedings of 8th Symposium on Intestinal Flora, Molecular Ecological Detection and Identification of Intestinal Microflora, edited by Tomotari Mitsuoka and Takahiro Matsuki), concretely, BiBIF-1: CCA CAT GAT CGC ATG TGA TT (SEQ ID NO:1) and BiBIF-2: CCGAAG GCT TGC TCC CAA A (SEQ ID NO:2), which are species-specific primers in the 16S rRNA region. The strain also has the ability to ferment galactose, glucose, fructose, lactose and gentiobiose.

*Bifidobacterium longum* No. 7 strain is a gram-positive, obligately anaerobic bacterium isolated from human adult feces and is a rod-shaped or branched polymorphic bacterium. The strain does not form spores and is nonmotile. When this bacterium is cultured on a BL agar (Eiken Chemical Co., Ltd.) plate at 37° C. for 48 hours by the steel wool method, opaque, circular, hemisphere, glossy colonies are formed. The strain has the ability to ferment arabinose, xylose, ribose, glucose, fructose, galactose, sucrose, maltose, lactose, melibiose, raffinose and melezitose.

*Bifidobacterium longum* OLB6290 strain is a gram-positive, obligately anaerobic, rod-shaped bacterium isolated from human infant feces and does not form spores. It has been confirmed that a PCR product is obtained by PCR using species-specific primers in the 16S rRNA region, BiLON-1: TTC CAG TTG ATC GCA TGG TC (SEQ ID NO:3) and BiLON-2: GGG AAG CCG TAT CTC TAC GA (SEQ ID NO:4). The strain has the ability to ferment arabinose, xylose, ribose, glucose, mannose, fructose, galactose, sucrose, maltose, lactose, melibiose, raffinose and melezitose.

A culture medium which is generally used as a culture medium for *Bifidobacterium* can be used for culturing the strain of the invention. That is, the culture medium which can be used for the invention is not particularly limited, and any culture medium can be used as long as the culture medium contains a main carbon source as well as a nitrogen source, inorganic substances and other nutrients in predetermined amounts.

As the carbon source, lactose, glucose, sucrose, fructose, starch hydrolysates, molasses and the like can be used depending on the assimilation of the strain used. As the nitrogen source, organic nitrogen-containing compounds such as casein hydrolysates, whey protein hydrolysates and soy protein hydrolysates can be used. In addition, meat extract, fish extract, yeast extract or the like is used as a growth stimulator.

The cultivation is preferably conducted under anaerobic conditions, and a known method such as a method in which the strain is cultured while blowing carbon gas can be used. The strain can be cultured also using another method, for example under microaerophilic conditions using a generally used liquid static culture process or the like or under batch culture conditions. The culture temperature is 25 to 50° C., particularly preferably 35 to 42° C. However, the culture temperature of the invention is not limited to the temperatures, and another temperature condition may also be used as long as the strain can grow at the temperature.

The pH of the culture medium is preferably kept at 6.0 to 7.0 during the cultivation, but another pH condition may also be used as long as the strain can grow at the pH. The culture period is preferably 3 to 48 hours, further preferably 8 to 24 hours, particularly preferably 10 to 20 hours, but another culture period may also be employed as long as the strain can grow in the culture period.

The agent of the invention (the anticariogenic agent, the agent for preventing periodontal disease and the agent for treating periodontal disease) or the composition of the invention (the anticariogenic composition, the composition for preventing periodontal disease and the composition for treating periodontal disease) contains a bifidobacterium, and the inventors have found that the bifidobacterium is a component having an anticariogenic effect and effects of preventing periodontal disease and treating periodontal disease, namely the active ingredient.

The bacterial cells obtained can be contained in the agent or the composition of the invention as a treated bifidobacterium product obtained by the following treatment. Examples of the treated bifidobacterium product include a culture after cultivation without any other treatment, a culture which has been centrifuged or filtered after cultivation, a concentrate thereof, a culture which has been further processed into paste, a dried product obtained by various methods (a spray dried product, a freeze dried product, a vacuum dried product, a drum dried product or the like), a liquid in which the cells are dispersed in a medium, a diluted product obtained using a diluent, a heat-treated product (heat-treated cells), a light-treated product (light-treated cells) obtained by treatment with ultraviolet rays and/or radiation, a chemically treated product (chemically treated cells) obtained by treatment with a chemical (germicide, an antibacterial agent or a bacteriostatic agent) and a pulverized product obtained by pulverizing a dried product with a mill or the like.

Centrifugation, filtration, concentration, pulverization and the like are conducted by generally used methods. The drying process can be conducted for example by vacuum drying, spray drying, freeze drying or drum drying. The medium, the diluent, the chemical (the germicide, the antibacterial agent or the bacteriostatic agent) and the like may be known ones, which are appropriately selected and used.

In the specification, such a treated product is sometimes simply referred to as "the treated bifidobacterium product" or "the treated product".

As described in the Examples below, it was found in the invention that cells of a bifidobacterium which have been inactivated for example by heat treatment at 90° C. for 15 minutes also have an anticariogenic effect, an effect of preventing periodontal disease and an effect of treating periodontal disease. Accordingly, the treated product containing the bacterial cells of the invention is useful, not only when the bacterial cells are viable cells but also when the bacterial cells are heat-treated cells (for example, when a sample of 0.1 ml is taken from a suspension (dispersed solution) of the heat-treated bifidobacterium cells and cultured under anaerobic conditions in a petri dish containing a culture medium in which the bifidobacterium can grow, colonies of the bifidobacterium are not formed).

The bifidobacterium and/or the treated product thereof obtained by the above methods can be contained in the agent of the invention in the form of viable cells or a treated product of pulverized or unpulverized cells after the heat treatment. Also, one kind thereof or a mixture of two or more kinds thereof may be contained in the agent of the invention.

In the form of viable bacterial cells, an effect of growing in the body (intestine) after the intake is expected. Also, heat-treated bacterial cells (for example, when a sample of 0.1 ml is taken from a suspension (dispersed solution) of the heat-treated bifidobacterium cells and cultured under anaerobic conditions in a petri dish containing a culture medium in which the bifidobacterium can grow, colonies of the bifidobacterium are not formed) are preferable because it is not necessary to consider that the bifidobacterium cannot live easily in the presence of oxygen and thus the agent of the invention can be used for a wider range of applications.

In particular, the bifidobacterium is particularly preferably in the form of heat-treated, non-viable cells. It is supposed that when the cells of the bifidobacterium are heat treated, the structure of the bifidobacterium cells and the like are changed, and the substance which contributes to the anticariogenic effect, the effect of preventing periodontal disease and the effect of treating periodontal disease is exposed easily.

Regarding the conditions of the heat treatment, for example, the heating temperature is generally 60 to 300° C., preferably 60 to 200° C., more preferably 60 to 150° C., further preferably 60 to 140° C., further preferably 60 to 130° C., further preferably 60 to 120° C., further preferably 60 to 110° C., further preferably 60 to 100° C., further preferably 70 to 100° C., further preferably 80 to 100° C., particularly preferably 85 to 95° C.

The heating temperature is preferably 60° C. or higher, because the viable cells of the bifidobacterium are killed. Also, the heating temperature is preferably 300° C. or lower because the bifidobacterium remains without being carbonized.

The heat treatment period is generally 0.01 to 120 minutes, preferably 0.015 to 60 minutes, more preferably 0.02 to 40 minutes, further preferably 0.025 to 30 minutes, further preferably 0.03 to 25 minutes, particularly preferably 0.03 to 20 minutes.

The heat treatment period is preferably 0.01 minutes or longer because the viable cells of the bifidobacterium are killed. Also, the heat treatment period is preferably 120 minutes or shorter because the viable cells can be killed efficiently while the thermal denaturation is prevented.

In the heat treatment in a low temperature range (60 to 100° C.), the optimal heat treatment period can be for example 0.2 to 120 minutes, preferably 0.2 to 60 minutes, more preferably 0.2 to 40 minutes, further preferably 0.2 to 30 minutes, further preferably 0.2 to 25 minutes, particularly preferably 0.2 to 20 minutes.

In the heat treatment in a high temperature range (100 to 300° C.), the optimal heat treatment period is for example 0.01 to 0.5 minutes, preferably 0.015 to 0.5 minutes, more preferably 0.02 to 0.5 minutes, further preferably 0.025 to 0.5 minutes, particularly preferably 0.03 to 0.5 minutes.

For example, the heat treatment of the bifidobacterium is conducted preferably at 90° C. for 15 minutes.

The heat treatment method is not particularly limited. For example, the bacterial cells obtained can be heated under predetermined conditions using a heat sterilizer such as a plate sterilizer, a tubular sterilizer, a direct heating-type sterilizer or a tank with a jacket.

The amount of the bifidobacteria that should be taken to obtain the anticariogenic effect, the effect of preventing periodontal disease and the effect of treating periodontal disease is for example, in order of preference, $10^8$ cells/day or more, $10^8$ to $10^{12}$ cells/day, $5\times10^8$ to $5\times10^{11}$ cells/day, $10^9$ to $10^{11}$ cells/day, $5\times10^9$ to $5\times10^{10}$ cells/day, $6\times10^9$ to $4\times10^{10}$ cells/day or $7\times10^9$ to $3\times10^{10}$ cells/day. The amount is more preferably $8\times10^9$ to $2\times10^{10}$ cells/day, further preferably $9\times10^9$ to $2\times10^{10}$ cells/day.

In the above range, the anticariogenic effect, the effect of preventing periodontal disease and the effect of treating periodontal disease are easily and actually obtained. In this regard, it was found that the agent of the invention (the anticariogenic agent, the agent for preventing periodontal disease and the agent for treating periodontal disease) is a component having anticariogenic effect and an effect of preventing periodontal disease and treating periodontal disease, namely the active ingredient. As long as the agent of the invention is in the form capable of exhibiting the effects, the purpose of use thereof is not limited.

Because the agent of the invention has few side effects, the agent of the invention can be taken continuously. To obtain the anticariogenic effect, the effect of preventing periodontal disease and the effect of treating periodontal disease, the intake period of the bifidobacterium of the invention is for example 2 to 10 weeks, 2 to 8 weeks, 3 to 7 weeks, 3.5 to 6.5 weeks or 4 to 6 weeks. The intake period is preferably 3.5 to 6.5 weeks, further preferably 4 to 6 weeks.

When the intake period of the bifidobacterium is in the above range, the anticariogenic effect, the effect of preventing periodontal disease and the effect of treating periodontal disease are easily and actually obtained. In particular, it is preferable that the bifidobacteria are applied in an amount of $10^8$ cells/day or more continuously for four weeks or longer, and it is more preferable that the bifidobacteria are applied in an amount of $10^{10}$ cells/day or more continuously for four weeks or longer.

The agent of the invention can be used alone and can also be used as an anticariogenic composition, a composition for preventing periodontal disease or a composition for treating periodontal disease by mixing the agent of the invention with another component. The amount of the agent of the invention in the composition can be determined optionally depending on the purpose, application, form, formulation, symptoms, body weight and the like.

Although the invention is not limited thereto, the agent of the invention can be contained in the composition in an amount of 0.01 to 99% (w/w), preferably 0.1 to 90% (w/w) relative to the total amount of the composition. Further preferably, the agent of the invention can be contained in an amount of 0.1 to 50% (w/w). This is because the intake (administration) becomes easy when the amount is in the range.

The agent or the composition of the invention can be administered orally or parenterally (intramuscularly, subcutaneously, intravenously, as a suppository, transdermally or the like). The subject who can take the agent or the composition of the invention may be an adult or may be an infant or an aged person. Also, the agent or the composition of the invention can be administered to a human who is highly sensitive to oligosaccharides or sugar alcohols without being affected by the sensitivity.

The agent or the composition of the invention has an anticariogenic effect, an effect of preventing periodontal disease and an effect of treating periodontal disease in addition to the known effects such as the improvement of diarrhea, the improvement of constipation, the prevention or the treatment of opportunistic bacterium infections and pathogenic microorganism infections, the inhibition of the growth of harmful enteric bacteria, the production of B vitamins, the facilitation of digestion and absorption by decomposing lactose, the improvement of the host intestinal immune system and the improvement in allergies.

Specifically, the composition of the invention can be used in the forms of both pharmaceutical product and of food or drink. It is expected that the composition of the invention exhibits an anticariogenic effect, an effect of preventing periodontal disease and an effect of treating periodontal disease when directly administered as a pharmaceutical product or directly taken as food for special dietary uses such as foods for specified health uses or nutritional food. Examples of the food for special dietary uses and the nutritional food include modified powdered milk, liquid food, food for a sick person, baby food including powdered infant formula, food for lactating women including powdered milk, supplements and enriched food.

When the agent of the invention is used as a pharmaceutical product, the route of administration is for example oral administration in the form of pharmaceutical preparation such as tablets, coated tablets, capsules, granules, powder, solutions, syrup or emulsions. An oral preparation containing an anticariogenic pharmaceutical composition can be obtained by preparing a pharmaceutical preparation of the bacterial cells and/or the treated product of the invention as the main drug according to a normal method using a known adjuvant which can be generally used in the field of pharmaceutical formulations, such as dispersants, excipients, binders, disintegrants, lubricants, colorants, flavoring agents, solubilizers, suspending agents and coating agents.

That is, because the oral preparation containing the pharmaceutical composition contains the agent of the invention, the oral preparation has an anticariogenic effect, an effect of preventing periodontal disease and an effect of treating periodontal disease in addition to the known effects such as the improvement of diarrhea, the improvement of constipation, the prevention or the treatment of opportunistic bacterium infections and pathogenic microorganism infections, the inhibition of the growth of harmful enteric bacteria, the production of B vitamins, the facilitation of digestion and absorption by decomposing lactose, the improvement of the host intestinal immune system and the improvement in allergies. Thus, the oral preparation is effective for various diseases such as diarrhea, constipation, opportunistic bacterium infections, pathogenic microorganism infections and diseases caused by the growth of harmful enteric bacteria and also effective for dental caries, periodontal disease and the like.

In particular, the agent of the invention is preferably used as a composition mixed with a dispersant. Examples of the dispersant include lactoproteins such as casein, soy protein, peptides, amino acids, starch, dextrin, xylan, oligosaccharides, saccharides (glucose, lactose, sucrose, galactose and maltose) and sugar alcohols (trehalose, xylitol, erythritol, palatinose, trehalulose and xylose). Dextrin is particularly preferable of the dispersants. This is because use of dextrin as the dispersant allows granulation of powder, easy handling during dispersion, dissolution or the like and long-term storage.

The dispersant, dextrin in particular, is preferably in the form of granules. This is because granules are highly soluble and can be packed well, and thus the composition can be divided into small portions. Also, granules have an advantage in production that the composition can be divided into portions accurately without variation in mass distribution by simply letting the composition fall on a packaging material.

In the composition of the invention, the mass ratio of the agent of the invention and the dispersant is preferably 1:100 to 1:2, more preferably 1:100 to 1:10, further preferably 1:100 to 1:20. This is because the agent of the invention can be dispersed efficiently when the mass ratio of the agent of the invention and the dispersant is in the range.

When the composition of the invention containing the agent of the invention and the dispersant (dextrin in particular) is orally administered for example, the composition of the invention can be administered as a package obtained by dividing the composition of the invention into small portions of a predetermined amount and packaging the portions in a packaging material. That is, the composition of the invention can be administered as a package containing the composition of the invention in a predetermined amount and a packaging material in which the composition is packaged in the packaging material. In the invention, it is preferable that each single dose is enclosed individually or two or more packaged portions correspond to a dose. It is particularly preferable that each dose is packaged individually.

When the agent or the composition of the invention is to be contained in an anticariogenic food composition without side effects, the agent or the composition of the invention may be added to various foods and drinks (milk, soft drinks, fermented milk, yogurt, cheese, bread, biscuits, crackers, pizza crust, modified powdered milk, liquid food, food for a sick person, baby food including powdered infant formula, food for lactating women including powdered milk, nutritional food and the like) and then taken. The agent and the composition of the invention can be used according to a normal method for general food compositions, for example by directly using the agent or the composition or mixing with other food or food components.

The state thereof may be any generally used state of foods and drinks such as solid (powder, granules and the like), paste, liquid or suspension. In such a form, the agent of the invention can be taken without psychological problems.

The agent and the composition of the invention can be used also as compositions containing water, protein, a carbohydrate, fat or oil, a vitamin, a mineral, an organic acid, an organic base, fruit juice, a flavoring agent or the like without side effects.

Examples of the protein include animal and vegetable proteins such as whole milk powder, skim milk powder, partially skimmed milk powder, casein, whey powder, whey protein, whey protein concentrate, separated whey protein, α-casein, β-casein, κ-casein, β-lactoglobulin, α-lactalbumin, lactoferrin, soy protein, hen's egg protein, meat protein and hydrolysates thereof; and milk-derived components such as butter, milk minerals, cream, whey, nonprotein nitrogen, sialic acid, phospholipids and lactose. All the kinds of protein and milk-derived components without side effects which have been used for pharmaceutical products and foods and drinks, can be used. A combination of two or more kinds of the components can also be used.

Examples of the carbohydrate include saccharides, modified starch (dextrin as well as soluble starch, British starch, oxidized starch, starch esters, starch ethers and the like) and dietary fibers.

Examples of the fat or oil include animal fats and oils such as lard, fish oils, fats and oils separated therefrom, hydrogenated fats and oils thereof and transesterified fats and oils thereof; and vegetable oils such as palm oil, safflower oil, corn oil, rapeseed oil, coconut oil, oils separated therefrom, hydrogenated oils thereof and transesterified oils thereof.

Examples of the vitamin include vitamin A, carotenes, B vitamins, vitamin C, D vitamins, vitamin E, K vitamins, vitamin P, vitamin Q, niacin, nicotinic acid, pantothenic acid, biotin, inositol, choline and folic acid.

Examples of the mineral include calcium, potassium, magnesium, sodium, copper, iron, manganese, zinc and selenium.

Examples of the organic acid include malic acid, citric acid, lactic acid and tartaric acid. All the organic acids without side effects which have been used for pharmaceutical products and foods and drinks can be used. A combination of two or more kinds of the components can also be used.

When the agent of the invention is provided as a food or a pharmaceutical preparation, the production method thereof may be a method known to one skilled in the art. One skilled in the art can produce a desired food or pharmaceutical preparation by appropriately combining a step of mixing the bifidobacterium or the treated product of the invention with other components, a forming step, a sterilization step, a fermentation step, a calcination step, a drying step, a cooling step, a granulation step, a enclosing step and the like.

The agent of the invention can also be applied also to food with health claims or food for a sick person. The system for food with health claims has been established not only for general foods but also for foods in the form of tablets, capsules and the like, in view of the trends inside and outside of Japan and also considering the consistency with the existing system for foods for specified health uses. The food with health claims includes foods for specified health uses (individual approval system) and foods with nutrient function claims (standard regulation system). It is expected that the anticariogenic effect is exhibited when food for special dietary uses such as foods for specified health uses or food with nutrient function claims containing the agent or the composition of the invention is directly taken.

EXAMPLES

Example 1

(Preparation of *Bifidobacterium*)

*Bifidobacterium bifidum* OLB6378 strain (accession number: NITE BP-31) was cultured at 37° C. overnight in an anaerobic EG medium having the composition shown in Table 1.

TABLE 1

| Component | Grams per liter of culture medium |
|---|---|
| Meat extract | 2.6 |
| Proteose peptone | 10 |
| Yeast extract | 5 |
| Sodium monohydrogen phosphate | 4 |
| Lactose | 1.5 |
| Soluble starch | 0.5 |
| L-cystine | 0.2 |
| L-cysteine hydrochloride | 0.5 |
| Defoaming agent (silicone) | 0.2 |
| Polysorbate 80 | 0.5 |
| Total | 25 |

After the cultivation, the cells were collected by centrifugation, and the residual medium components were washed away with sterilized water. Then, the cells were freeze dried. The cells obtained here were used as raw OLB6378 cell powder.

Example 2

(Preparation of the Agent of the Invention)
a) Preparation of Freeze Dried Powder of Heat-Treated OLB6378 Cells The raw OLB6378 cell powder obtained in Example 1 (number of viable cells of $3.9 \times 10^{11}$ cfu/g) in an amount of 180 g was completely suspended in 2800 ml of raw material water adjusted at 45° C. by stirring. Then, the suspension was heated while stirring the suspension, kept at 90° C. for 15 minutes and cooled. The suspension of the heated cells obtained was freeze dried, and 156 g of freeze dried powder of heat-treated OLB6378 cells was obtained. No viable bifidobacterium cells were observed when the heat-treated OLB6378 cells were cultured on an MRS agar plate. Also, in the 156 g of freeze dried powder of heat-treated OLB6378 cells obtained, $7.02 \times 10^{13}$ of the bifidobacterium cells are approximately present ($3.9 \times 10^{11}$ cfu/g$\times 180$ g=$7.02 \times 10^{13}$ cfu). This heated cell number is represented in terms of a viable cell number (cfu).

b) Preparation of the Agent of the Invention

The freeze dried powder of the heat-treated OLB6378 cells in an amount of 120 g and 2880 g of dextrin granules (Matsutani Chemical Industry Co., Ltd.) were mixed thoroughly, and the mixture was divided into portions of 1 g. The agent of the invention was thus prepared. In the agent of the invention, $1.8 \times 10^{10}$ of the bifidobacterium cells are approximately present ($7.02 \times 10^{13}$ cfu/156 g$\times 120$ g/3000 g=$1.8 \times 10^{10}$ cfu). This heated cell number is represented in terms of a viable cell number (cfu).

Comparative Example 1

(Preparation of Placebo)

The placebo of Comparative Example 1 was prepared by dividing 3000 g of dextrin granules (Matsutani Chemical Industry Co., Ltd.) into portions of 1 g as a replacement for the agent of Example 2.

Test Example 1

In Test Example 1, the group of subjects who received the agent of Example 2 was named "the invention's agent group", and the group of subjects who received the placebo of Comparative Example 1 was named "the placebo group". Thirty subjects in total for the two groups were selected according to the subject selection criteria and the subject exclusion criteria described below. Fifteen subjects were assigned to the invention's agent group, and the remaining 15 subjects were assigned to the placebo group. The subjects in both groups received the agent of Example 2 or the placebo of Comparative Example 1 twice a day. The intake period was five weeks. Both groups were evaluated as described in the evaluation items below.

<Subject Selection Criteria

The subject selection criteria were as follows. Subjects who satisfied all of A) to E) below were selected.

A) Females aged 20 to 40.

B) Generally have three meals a day.

C) Labial/buccal surfaces of four or more of the following six teeth (according to FDI numbering system) are measurable: 16 (maxillary right first molar); 21 (maxillary left central incisor); 24 (maxillary left first premolar); 36 (mandibular left first molar); 41 (mandibular right central incisor); and 44 (mandibular right first premolar). Teeth with the FDI numbers of 17, 15, 11, 22, 25, 37, 35, 31, 42 and 45 are present as alternative to the six representative teeth.

D) Subjects who have 20 teeth or more and have no treatment of dental caries and periodontal disease at the time of screening test.

E) Subjects who are given a full explanation of the purpose and the contents of the test and who are capable of consenting. Subjects who are willing to voluntary participate in the test with full understanding and who give written consent to participate in the test.

<Subject Exclusion Criteria>

The subject exclusion criteria were as follows. Persons who satisfied at least one of a) to j) below were excluded.

a) Diagnosed as dental caries (C3 or higher) or severe periodontal disease at the screening test.

b) Having diabetes, chronic renal disease, gastrointestinal dysfunction, pulmonary disease, malignant tumor or the like and receiving any medications.

c) Participation or intention to participate in another test of a pharmaceutical product or food or the like.

d) Amount of stimulated salivation for five minutes of 3.0 ml or less.

e) pH of stimulated saliva of 6.2 or less.

f) Use of a removable bridge.

g) Use/intake of a mouthwash, an antibiotic or an antibacterial agent or visit to a dentist within one month of the screening test.

h) Food allergies.

i) Women who are pregnant, plan a pregnancy during the test period or breast-feeding.

j) Any other person who the dentist in charge of the test determines to be inadequate as a subject for the test.

<Evaluation Items>

1. Proportion of Cariogenic Bacteria

The proportion of cariogenic bacteria is an indicator of whether the agent of the invention has anticariogenic effect and is the proportion of mutans streptococci in streptococci in the saliva. That is, the proportion of cariogenic bacteria is represented by the following equation.

Proportion of cariogenic bacteria=(Number of mutans streptococci/Number of streptococci)×100

Stimulated saliva samples (saliva secreted while chewing gum) were collected for five minutes from the subjects belonging to the invention's agent group and the placebo group. The numbers of mutans streptococci and the numbers of streptococci in the saliva samples were measured by the cultivation method, and the proportions of cariogenic bacteria were calculated. The proportions of cariogenic bacteria were measured on the first day of intake and four weeks and five weeks after starting the intake. The number of streptococci was determined by counting the colonies that were formed when a certain amount of a saliva sample, which had been diluted appropriately, was cultured on a Mitis-Salivarius (MS) agar plate under anaerobic conditions at 37° C. for 48 hours. The number of mutans streptococci was determined in the same manner but using a Mitis-Salivarius agar plate containing bacitracin (SIGMA) (MSB medium).

2. Gingival Index

The gingival index is an indicator of whether the agent of the invention has an effect of preventing periodontal disease and an effect of treating periodontal disease. The gingival index was measured by the method described in Non-Patent Document 1 (Periodontal disease in pregnancy. Lee H, Silness J., Acta Odontologica Scandinavica 1963 21: 533-51). Specifically, the lingual, labial/buccal, mesial and distal surfaces of predetermined six teeth (24 surfaces in total) were observed visually, and the gingival index was determined by the criteria and the method described below. In this regard, the predetermined six teeth were the maxillary right first molar, the maxillary left central incisor, the maxillary left first premolar, the mandibular left first molar, the mandibular right central incisor and the mandibular right first premolar.

Criterion

0: Clinically normal gingiva.

1: Mild inflammation and slight change in color of gingiva, but no bleeding from the inner gingival margin on probing.

2: Moderate inflammation, edema and glazing of gingiva with redness, and bleeding from the inner gingival margin on probing.

3: Severe inflammation, marked redness and edema, spontaneous bleeding and ulceration.

Method

After the stimulated saliva samples (saliva secreted while chewing gum) were collected for five minutes from the subjects, the gingival indexes were calculated from the records of the dentist's questions and the oral diagnosis. The gingival indexes were calculated by the following equation on the screening date (one month before starting the intake) and five weeks after starting the intake.

(Gingival index)=(Total score of gingival evaluation of all teeth)/(Number of tested tooth surfaces)

3. Plaque Index

The plaque index is an indicator of whether the agent of the invention has an effect of preventing periodontal disease and an effect of treating periodontal disease. The plaque index was measured by the method described in Non-Patent Document 2 (Comparative cleaning efficiency of manual and power brushing. Quigley H, Hein J N., J Am Dent Ass 1962 65: 26). Specifically, the lingual, labial/buccal, mesial and distal surfaces of predetermined six teeth (24 surfaces in total) were observed visually, and the plaque index was determined by the criteria and the method described below. In this regard, the predetermined six teeth were the maxillary right first molar, the maxillary left central incisor, the maxillary left first premolar, the mandibular left first molar, the mandibular right central incisor and the mandibular right first premolar.

Criteria

0: No plaque adhesion.

1: Spots of plaque along the gingival margin.

2: Line of plaque along the gingival margin.

3: Plaque covering not more than one third of the tooth surface at the gingival side.

4: Plaque covering not more than two thirds of the tooth surface at the gingival side.

5: Plaque covering two thirds or more of the tooth surface at the gingival side.

Method

After the stimulated saliva samples (saliva secreted while chewing gum) were collected for five minutes from the subjects, the plaque indexes were calculated from the records of the dentist's questions and the oral diagnosis. The plaque indexes were calculated by the following equation on the screening date (one month before starting the intake) and five weeks after starting the intake.

(Plaque index)=(Total score of plaque evaluation of all teeth)/(Number of tested tooth surfaces)

Results and Discussion

1. Proportion of Cariogenic Bacteria

In the invention's agent group, the average proportion of cariogenic bacteria was 0.5 on the first day of intake, and the average proportion of cariogenic bacteria decreased significantly to 0.2 after four weeks. On the other hand, in the placebo group, the average proportion of cariogenic bacteria was 0.2 on the first day of intake, but the average proportion of cariogenic bacteria did not change significantly and remained 0.2 after four weeks.

The values of the invention's agent group and the placebo group were statistically analyzed to compare the values between the groups (the Wilcoxon rank-sum test for the comparison between the groups, and the Wilcoxon signed-rank test for the comparison of the values before and after the intake period within the groups). As a result, the p value on the first day of intake was 0.218, and the p value after four weeks was 0.973.

2. Gingival Index

In the invention's agent group, the average gingival index was 0.13 on the first day of intake, and the average gingival index decreased significantly to 0.04 after five weeks. On the other hand, in the placebo group, the average gingival index was 0.21 on the first day of intake, but the average gingival index did not decrease significantly and was 0.505 after five weeks.

The values of the invention's agent group and the placebo group were statistically analyzed to compare the values between the groups (the Wilcoxon rank-sum test for the comparison between the groups, and the Wilcoxon signed-rank test for the comparison of the values before and after the intake period within the groups). As a result, the p value on the screening day was 0.378, and the p value after five weeks was 0.065.

3. Plaque Index

In the invention's agent group, the average plaque index was 0.17 on the first day of intake, and the average plaque index did not increase significantly and remained 0.17 after five weeks. On the other hand, in the placebo group, the average plaque index was 0.17 on the first day of intake, but the average plaque index increased significantly to 0.33 after five weeks.

The values of the invention's agent group and the placebo group were statistically analyzed to compare the values between the groups (the Wilcoxon rank-sum test for the comparison between the groups, and the Wilcoxon signed-rank test for the comparison of the values before and after the intake period within the groups). As a result, the p value on the screening day was 0.849, and the p value after five weeks was 0.043.

As shown by the results, a significant decrease in the proportion of cariogenic bacteria was observed in the invention's agent group only, but not in the placebo group. Thus, it was found that the agent of the invention has anticariogenic effect.

Also, a significant decrease in the gingival index and prevention of a deterioration in the plaque index were observed in the invention's agent group only, but not in the placebo group. Therefore, it was found that the agent of the invention has an effect of preventing periodontal disease and an effect of treating periodontal disease.

Although the invention has been explained in detail using specific embodiments, it is obvious to one skilled in the art that various changes and modifications can be made without departing from the purpose and the scope of the invention. The present application is based on a Japanese patent application filed on May 29, 2015 (patent application No. 2015-110743), and the entire contents thereof are incorporated in the invention by reference.

INDUSTRIAL APPLICABILITY

According to the invention, a novel anticariogenic agent or anticariogenic composition containing a bifidobacterium and without side effects can be provided. Also, a novel agent for preventing periodontal disease or for treating periodontal disease containing a bifidobacterium and without side effects or a novel composition for preventing periodontal disease or for treating periodontal disease containing a bifidobacterium and without side effects can be provided. The bifidobacterium can decrease the proportion of cariogenic bacteria in the oral cavity and as a result can prevent and treat dental caries. Also, the bifidobacterium can reduce the symptoms of gingivitis and can reduce the adhesion of plaque to teeth. As a result, the bifidobacterium can prevent and treat periodontal disease.

---

What is claimed is:

1. A method of treating periodontal disease comprising:
orally administering an amount of an agent comprising *Bifidobacterium bifidum* OLB6378 strain having the accession number NITE BP-31 to a subject in need thereof, wherein the *Bifidobacterium bifidum* OLB6378 strain having the accession number NITE BP-31 is in the form of non-viable cells.

2. The method according to claim 1, wherein the *Bifidobacterium bifidum* cells is in the form of are heat-treated cells.

3. The method according to claim 1, wherein the agent administered to the subject comprises $10^8$ cells of the *Bifidobacterium bifidum* cells and the administration is per day or more continuously for four weeks or longer.

4. The method according to claim 3, wherein the administration is per day or more continuously for four to six weeks.

5. The method according to claim 1, wherein the agent administered to the subject comprises $10^9$ to $10^{11}$ cells of the *Bifidobacterium bifidum* cells and the administration is per day continuously for four weeks.

6. The method according to claim 1, wherein the agent further comprises a dispersant.

7. The method according to claim 6, wherein the agent is a food composition comprising the dispersant.

8. The method according to claim 7, wherein the dispersant is dextrin.

9. The method according to claim 1, wherein the subject is human.

* * * * *